US011525992B2

(12) United States Patent
Lee et al.

(10) Patent No.: US 11,525,992 B2
(45) Date of Patent: Dec. 13, 2022

(54) STEREO MICROSCOPE, OPTICAL DEVICE, AND METHOD FOR FORMING OPTICAL PATH USING SAME

(71) Applicant: KOH YOUNG TECHNOLOGY INC., Seoul (KR)

(72) Inventors: Chan Kwon Lee, Ansan-si (KR); Young Chul Park, Seoul (KR); Yu Ri Koh, Seoul (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 499 days.

(21) Appl. No.: 16/635,842

(22) PCT Filed: Apr. 9, 2018

(86) PCT No.: PCT/KR2018/004151
§ 371 (c)(1),
(2) Date: Jan. 31, 2020

(87) PCT Pub. No.: WO2019/027123
PCT Pub. Date: Feb. 7, 2019

(65) Prior Publication Data
US 2020/0264420 A1 Aug. 20, 2020

(30) Foreign Application Priority Data
Jul. 31, 2017 (KR) .......................... 10-2017-0096942

(51) Int. Cl.
*G02B 21/22* (2006.01)
*A61B 5/00* (2006.01)
(Continued)

(52) U.S. Cl.
CPC ............ *G02B 21/22* (2013.01); *A61B 5/0066* (2013.01); *A61B 5/0084* (2013.01);
(Continued)

(58) Field of Classification Search
None
See application file for complete search history.

(56) References Cited

U.S. PATENT DOCUMENTS 4,783,159 A 11/1988 Takagi et al.
6,563,113 B1 5/2003 Amann et al.
(Continued)

FOREIGN PATENT DOCUMENTS

CN 101273918 10/2008
CN 102928971 2/2013
(Continued)

OTHER PUBLICATIONS

Extended European Search Report, corresponding to European Application No. /Patent No. 18841333.0, dated Apr. 15, 2021.
(Continued)

*Primary Examiner* — Nancy Bitar
(74) *Attorney, Agent, or Firm* — Kile Park Reed & Houtteman PLLC

(57) ABSTRACT

The present disclosure relates to a medical microscope field. A stereo microscope connected to an optical coherence tomography (OCT) unit for forming a tomographic image of a target object includes an objective lens unit including a plurality of lenses each having an aperture of a predetermined size, a pair of first magnification lens units each including a plurality of lenses having a pair of magnification lens apertures positioned within the aperture of the objective lens unit, a second magnification lens unit including a plurality of lenses having an OCT aperture disposed separately from the pair of magnification lens aperture within the aperture of the objective lens unit, and a light delivery unit configured to receive light from the OCT unit and deliver the
(Continued)

light to the second magnification lens unit and configured to deliver light received from the second magnification lens unit to the OCT unit.

11 Claims, 4 Drawing Sheets

(51) Int. Cl.
    *G02B 21/02*     (2006.01)
    *G02B 21/36*     (2006.01)
    *G06T 11/00*     (2006.01)

(52) U.S. Cl.
    CPC ......... *G02B 21/025* (2013.01); *G02B 21/361* (2013.01); *G06T 11/003* (2013.01); *A61B 2562/0242* (2013.01); *G06T 2207/10056* (2013.01); *G06T 2207/10101* (2013.01)

(56) References Cited

U.S. PATENT DOCUMENTS

| | | | |
|---|---|---|---|
| 2008/0117432 A1 | 5/2008 | Reimer et al. |
| 2008/0239473 A1 | 10/2008 | Takagi |
| 2009/0279052 A1 | 11/2009 | Hauger et al. |
| 2010/0309478 A1 | 12/2010 | Reimer et al. |
| 2012/0169862 A1 | 7/2012 | Son et al. |
| 2014/0029089 A1 | 1/2014 | Guentert |
| 2018/0035887 A1 | 2/2018 | Nakanishi et al. |

FOREIGN PATENT DOCUMENTS

| | | |
|---|---|---|
| CN | 103576305 | 2/2014 |
| DE | 10 2008 041 284 | 11/2009 |
| EP | 1 918 755 | 5/2008 |
| JP | 2001-142003 | 5/2001 |
| JP | 2001-516071 | 9/2001 |
| JP | 2001516071 | * 9/2001 |
| JP | 2006-280805 | 10/2006 |
| JP | 2008-268852 | 11/2008 |
| JP | 2014-026285 | 2/2014 |
| JP | 2016206348 | * 8/2016 |
| JP | 2016-202452 | 12/2016 |
| JP | 2016-202453 | 12/2016 |
| JP | 2016-206348 | 12/2016 |
| KR | 10-2012-0077123 | 7/2012 |

OTHER PUBLICATIONS

Chinese Office Action, with English translation, corresponding to Chinese Application No. or Publication No. 201880050131.7, dated Apr. 30, 2021.
Japanese Office Action with English translation for Japanese Patent Application No. 2020-505379, dated Sep. 21, 2021.
Chinese Office Action with English translation for Chinese Application No. or Publication No. 201880050131.7, dated Nov. 18, 2021.
Japanese Office Action, with English translation, corresponding to Japanese Patent Application No. 2020-505379, dated Feb. 2, 2021.
International Search Report with English translation corresponding to International Application No. PCT/KR2018/004151, dated Jul. 31, 2018.
Korean Office Action, with English translation, corresponding to Application No. 10-2017-0096942, dated Mar. 21, 2018.

* cited by examiner

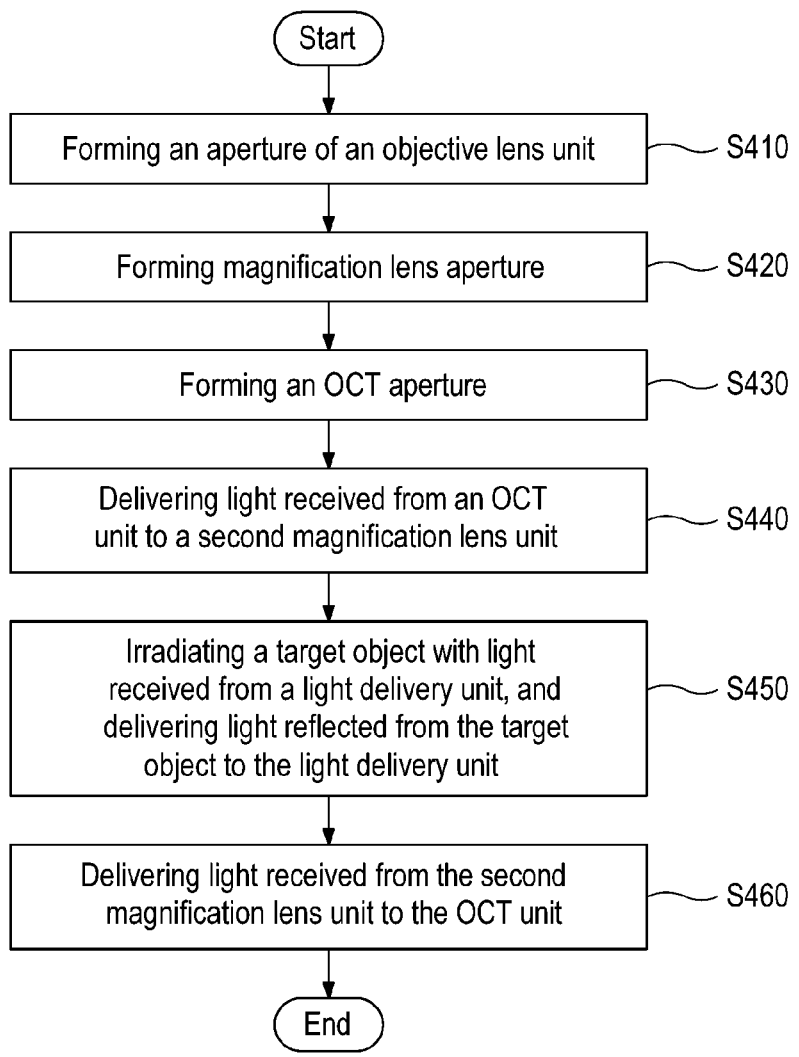

STEREO MICROSCOPE, OPTICAL DEVICE, AND METHOD FOR FORMING OPTICAL PATH USING SAME

TECHNICAL FIELD

The present disclosure relates to a stereo microscope, an optical device, and a method for forming an optical path using same.

BACKGROUND

A microscope is an optical device capable of forming an optical image in which a target object is magnified. In particular, a stereo microscope includes optical systems corresponding to both eyes and may form a stereoscopic image of a target object.

An optical coherence tomography (OCT) device is an optical device that can form a tomographic image of a target object using an interference phenomenon of light. In an early stage of development, the OCT device could acquire tomographic images of several frames per second while mechanically changing an optical path. In recent years, the OTC device is capable of forming tomographic images of hundreds of frames per second using a tunable laser.

In general, the stereo microscope is used to observe a three-dimensional shape of an appearance of a target object. The OCT device can form three-dimensional tomographic images up to a certain depth from a surface of a target object and, therefore, can be used to observe an internal structure of the target object.

SUMMARY

In the medical field, a stereo microscope may be used to observe an appearance of a target object such as, for example, a portion of a body of a patient during surgery. In this case, during surgery, additional devices are required for more precise inspection of an internal structure as well as an appearance of a particular object.

According to one embodiment of the present disclosure, there is provided a stereo microscope to which an optical coherence tomography (OCT) unit for forming a tomographic image of a target object is connectable, including: an objective lens unit including a plurality of lenses each having an aperture of a predetermined size; a pair of first magnification lens units each including a plurality of lenses having a pair of magnification lens apertures and positioned within the aperture of the objective lens unit; a second magnification lens unit including a plurality of lenses having an optical coherence tomography (OCT) aperture and disposed separately from the pair of magnification lens apertures within the aperture of the objective lens unit; and a light delivery unit configured to receive light from the OCT unit and deliver the light to the second magnification lens unit and configured to deliver light received from the second magnification lens unit to the OCT unit, wherein the second magnification lens unit is configured to irradiate the target object with light received from the light delivery unit and deliver light reflected from the target object to the light delivery unit.

In one embodiment, the pair of first magnification lens units and the second magnification lens unit may include separately-arranged body tubes configured to surround side surfaces of the plurality of lenses of the pair of first magnification lens units and side surfaces of the plurality of lenses of the second magnification lens unit, respectively.

In one embodiment, the pair of magnification lens apertures may be disposed at positions symmetrical with respect to an optical axis of the objective lens unit, the OCT aperture may be disposed to be spaced apart from an axis connecting the pair of magnification lens apertures, and a normal line extending from the OCT aperture to the axis may be configured to intersect the optical axis.

In one embodiment, the light delivery unit may include at least one of a folding mirror, a beam splitter, and a prism.

In one embodiment, the stereo microscope may further include: an illumination unit having an aperture spaced apart from the pair of magnification lens apertures and the OCT aperture within the aperture of the objective lens unit.

In one embodiment, the stereo microscope may further include: a pair of ocular lens units on which a stereoscopic image of the target object received through the pair of first magnification lens units is formed, wherein the light delivery unit may be disposed between the pair of ocular lens units and the second magnification lens unit.

According to another embodiment of the present disclosure, there is provided an optical device, including: an optical coherence tomography (OCT) unit configured to form a tomographic image of a target object; and a stereo microscope configured to form a stereoscopic image of the target object, wherein the stereo microscope includes: a target objective lens unit including a plurality of lenses each having an aperture of a predetermined size; a pair of first magnification lens units each including a plurality of lenses having a pair of magnification lens apertures and positioned within the aperture of the objective lens unit; a second magnification lens unit including a plurality of lenses having an OCT aperture and disposed separately from the pair of magnification lens apertures within the aperture of the objective lens unit; and a light delivery unit configured to receive light from the OCT unit and deliver the light to the second magnification lens unit and configured to deliver light received from the second magnification lens unit to the OCT unit, wherein the second magnification lens unit is configured to irradiate the target object with light received from the light delivery unit and deliver light reflected from the target object to the light delivery unit.

In one embodiment, the pair of first magnification lens units and the second magnification lens unit may include separately-arranged body tubes configured to surround side surfaces of the plurality of lenses of the pair of first magnification lens units and side surfaces of the plurality of lenses of the second magnification lens unit, respectively.

In one embodiment, the pair of magnification lens apertures may be disposed at positions symmetrical with respect to an optical axis of the objective lens unit, the OCT aperture may be disposed to be spaced apart from an axis connecting the pair of magnification lens apertures, and a normal line extending from the OCT aperture to the axis may be configured to intersect the optical axis.

In one embodiment, the light delivery unit may include at least one of a folding mirror, a beam splitter, and a prism.

In one embodiment, the stereo microscope may further include an illumination unit having an aperture spaced apart from the pair of magnification lens apertures and the OCT aperture within the aperture of the objective lens unit.

In one embodiment, the stereo microscope may further include a pair of ocular lens units on which a stereoscopic image of the target object received through the pair of first magnification lens units is formed, and the light delivery unit may be disposed between the pair of ocular lens units and the second magnification lens unit.

According to a further embodiment of the present disclosure, there is provided an optical path forming method for forming a stereoscopic image and a tomographic image of a target object, including: forming, by an objective lens unit, an aperture of a predetermined size; forming, by a first magnification lens unit, a magnification lens aperture so as to be positioned within the aperture of the objective lens unit; forming, by a second magnification lens unit, an optical coherence tomography (OCT) aperture positioned within the aperture of the objective lens unit and disposed separately from the pair of magnification lens apertures; delivering, by a light delivery unit, light received from an OCT unit for forming the tomographic image of the target object to the second magnification lens unit; irradiating, by the second magnification lens unit, the target object with light received from the light delivery unit, and delivering, by the second magnification lens unit, light reflected from the target object to the light delivery unit; and delivering, by the light delivery unit, light received from the second magnification lens unit to the OCT unit.

According to various embodiments of the present disclosure, it is possible to freely adjust the insertion position and the size of the light delivery unit used to form the tomographic image in the OCT unit without interference of the optical system used to form the stereoscopic image in the stereo microscope.

In addition, according to various embodiments of the present disclosure, it is possible to suppress performance degradation which may be caused by sharing the magnification lens unit in the stereo microscope and the OCT unit that make use of light having different wavelengths.

BRIEF DESCRIPTION OF DRAWINGS

FIG. 4 is a flowchart illustrating a procedure of an optical path forming method for forming a stereoscopic image and a tomographic image of a target object according to one embodiment of the present disclosure.

DETAILED DESCRIPTION

Figure 1:
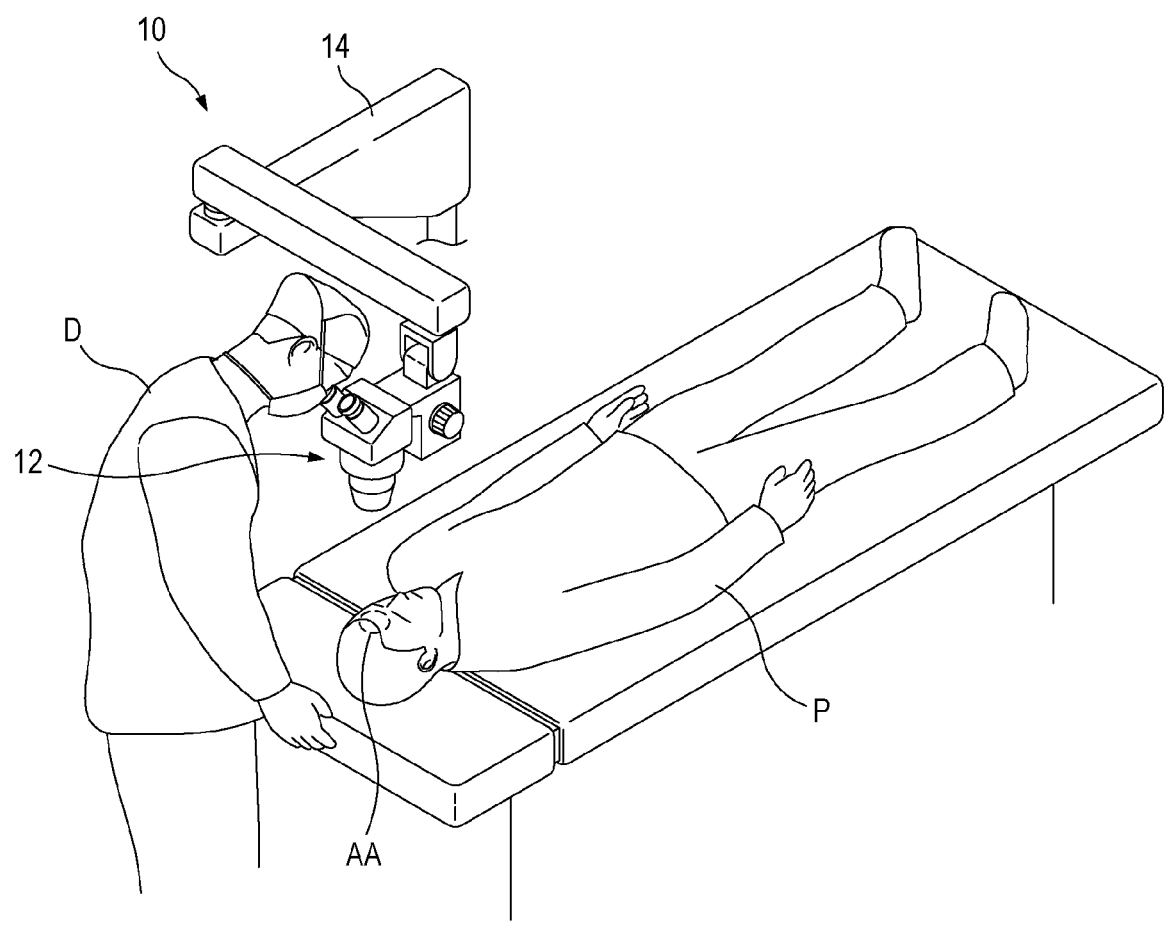
FIG. 1 is an exemplary view illustrating a usage environment of an optical device according to one embodiment of the present disclosure.

Embodiments of the present disclosure are illustrated for describing the present disclosure. Embodiment of the present disclosure may be implemented in various forms, and the present disclosure is not construed as being limited to the embodiments illustrated below or to the detailed descriptions of these embodiments.

The term "unit" used in these embodiments means a software component or a hardware component, such as a field-programmable gate array (FPGA) and an application-specific integrated circuit (ASIC). However, a "unit" is not limited to software and hardware but may be configured to be an addressable storage medium or may be configured to run on one or more processors. For example, a "unit" includes components, such as software components, object-oriented software components, class components, and task components, as well as processors, functions, attributes, procedures, subroutines, segments of program codes, drivers, firmware, micro-codes, circuits, data, databases, data structures, tables, arrays, and variables. Functions provided in components and "units" may be combined into a smaller number of components and "units" or may be further subdivided into additional components and "units."

All technical or scientific terms used herein have meanings that are generally understood by a person having ordinary knowledge in the art to which the present disclosure pertains, unless otherwise specified. The terms used herein are selected only for a more clear illustration of the present disclosure, and are not intended to limit the scope of claims in accordance with the present disclosure.

A singular expression used herein can include meanings of plurality, unless otherwise mentioned, and the same is applied to a singular expression stated in the claims.

The terms "first", "second", etc. used herein are used to identify a plurality of components from one another, and are not intended to limit the order or importance of the relevant components.

The expressions "include", "provided with", "have" and the like used herein should be understood as open-ended terms connoting the possibility of inclusion of other embodiments, unless otherwise mentioned in a phrase or sentence including the expressions.

The expressions "based on" and "on the basis of" used herein are used to describe one or more factors that influences a decision, an action of judgment, or an operation described in a phrase or sentence including the relevant expression, and this expression does not exclude additional factors influencing the decision, the action of judgment or the operation.

When a certain component is described as "coupled to" or "connected to" another component, this should be understood as having a meaning that the certain component may be coupled or connected directly to the other component or that the certain component may be coupled or connected to the other component via a new intervening component.

Hereinafter, embodiments of the present disclosure will be described with reference to the accompanying drawings. In the accompanying drawings, like or relevant components are indicated by like reference numerals. In the following description of embodiments, repeated descriptions of the identical or relevant components will be omitted.

FIG. 1 is an exemplary view illustrating a usage environment of an optical device according to one embodiment of the present disclosure.

As shown in FIG. 1, a doctor D may examine a target object, for example a lesion AA of a patient P, before or after surgery for the patient P, using an optical device 10. In one embodiment, the doctor D may perform an examination of the lesion AA using the optical device 10 without separating the lesion AA from the patient P. In another embodiment, the doctor D may perform an examination of a portion of the lesion AA using the optical device 10 by separating a portion of the lesion AA from the patient P.

The optical device 10 may include a stereo microscope 12 capable of forming a stereoscopic image of the lesion AA of the patient P and an Optical Coherence Tomography (OCT) unit 14 capable of forming a tomographic image of the lesion AA of the patient P. In one embodiment, the doctor D may examine an appearance of the lesion AA of the patient P using the stereo microscope 12. In this case, if it is determined during the appearance examination using the stereo microscope 12 that a more precise examination (e.g., histological examination) of the internal structure is necessary, a stereoscopic tomographic image for the lesion AA of the patient P may be formed by using the OCT unit 14.

Figure 2:
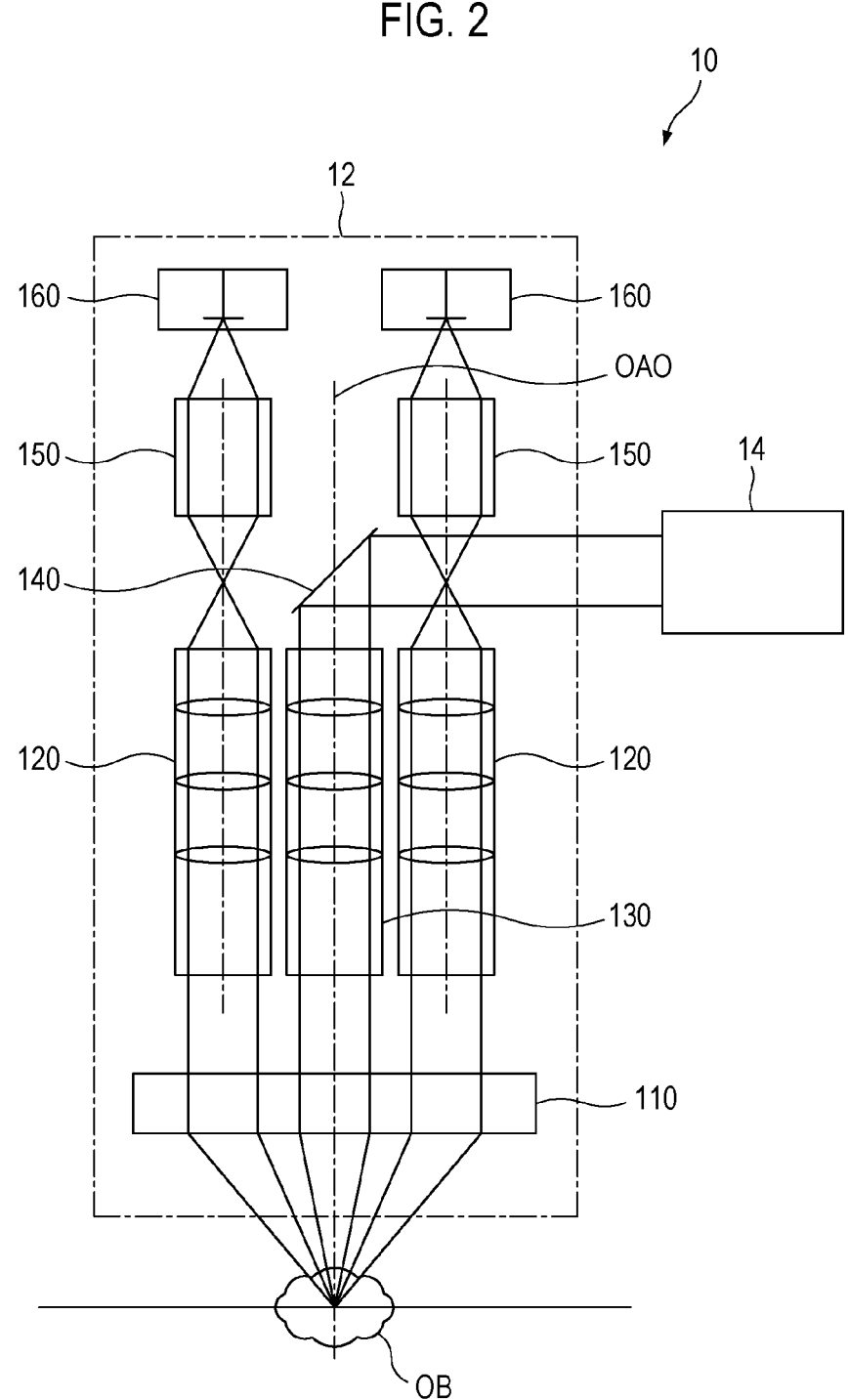
FIG. 2 is an exemplary view illustrating a configuration of the optical device according to one embodiment of the present disclosure.

FIG. 2 is an exemplary view illustrating a configuration of the optical device according to one embodiment of the present disclosure.

As shown in FIG. 2, the optical device 10 may include a stereo microscope 12 for forming a stereoscopic image of a target object OB and an OCT unit 14 for forming a tomographic image of the target object OB. The OCT unit 14 may be connected to or coupled with the stereo microscope 12 to form a tomographic image of the target object OB. In one embodiment, the stereo microscope 12 may include an objective lens unit 110, a pair of first magnification lens units 120, a second magnification lens unit 130, a light delivery unit 140, a pair of tube lens units 150, and a pair of ocular lens units 160. However, this is only for the purpose of description. The present disclosure is not limited thereto. Various lenses may be included in the optical device 10.

The objective lens unit 110 may be configured by a plurality of lenses each having an aperture of a predetermined size. The objective lens unit 110 may perform a function of changing a focal length of a plurality of lenses to adjust a working distance that indicates a distance from the objective lens unit 110 to the target object OB. Further, the objective lens unit 110 may form an optical axis OAO. The optical axis OAO of the objective lens unit 110 may be defined by a line that connects the curvature centers of the respective lens surfaces of the plurality of lenses included in the objective lens unit 110.

Each of the pair of first magnification lens units 120 may be configured by a plurality of lenses, and may have a pair of magnification lens apertures located within the aperture of the objective lens unit 110. The first magnification lens units 120 may perform a function of adjusting the focus of the stereoscopic image of the target object OB by changing the magnification. In one embodiment, the plurality of lenses included in the pair of first magnification lens units 120 may be subjected to anti-reflective (AR) coating, magnification adjustment or the like so that they can operate in a wavelength region of visible light (e.g., 380 nm to 800 nm) for forming a stereoscopic image of the target object OB.

The second magnification lens unit 130 may be configured by a plurality of lenses having an optical coherence tomography (OCT) aperture disposed separately from the pair of magnification lens apertures within the aperture of the objective lens unit 110. The second magnification lens unit 130 may perform a function of adjusting the focus of the tomographic image of the target object OB by changing the magnification. Further, the second magnification lens unit 130 may irradiate the light received from the light delivery unit 140 to the target object OB through the objective lens unit 110, and may deliver the light reflected from the target object OB and delivered through the objective lens unit 110 to the light delivery unit 140. In one embodiment, the plurality of lenses included in the second magnification lens unit 130 may be subjected to the AR coating, the magnification adjustment or the like so that they can operate in a wavelength region of infrared light (e.g., 700 nm to 14 μm) for forming a tomographic image of the target object OB.

The light delivery unit 140 may receive light from the OCT unit 14, may deliver the light to the second magnification lens unit 130, and may deliver the light received from the second magnification lens unit 130 to the OCT unit 14. In FIG. 2, the light delivery unit 140 is shown to be positioned between the pair of tube lens units 150 and the second magnification lens unit 130. However, the light delivery unit 140 may be located between the pair of ocular lens unit 160 and the pair of tube lens unit 150, or may be located between the pair of ocular lens unit 160 and the second magnification lens unit 130 at an arbitrary position that does not overlap an optical system for the stereo microscope 12. In one embodiment, the light delivery unit 140 may include a folding mirror, a beam splitter, a prism, and the like. However, this is only for the purpose of description. The present disclosure is not limited thereto. Various devices capable of refracting light may constitute the light delivery unit 140.

The pair of tube lens units 150 may deliver the light received from the pair of first magnification lens units 120 to the pair of ocular lens units 160. The pair of ocular lens units 160 may allow the stereoscopic image of the target object OB to be formed respectively based on the light received from the pair of tube lens units 150. A user of the optical device 10 such as the doctor D or the like may confirm the stereoscopic image of the target object OB formed respectively on the pair of ocular lens units 160 using both eyes.

Figure 3:
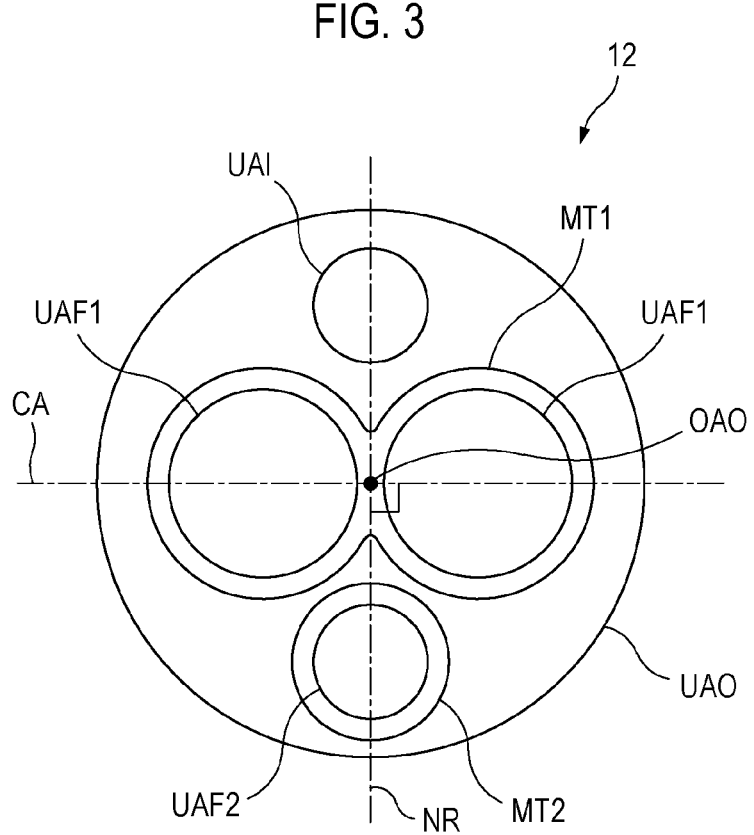
FIG. 3 is a conceptual diagram illustrating each aperture of the optical device according to one embodiment of the present disclosure.

FIG. 3 is a conceptual diagram illustrating each aperture of the optical device according to one embodiment of the present disclosure.

As shown in FIG. 3, the objective lens unit 110 may be configured to form an aperture UAO of a predetermined size. Further, the pair of first magnification lens units 120 may be configured to form a pair of magnification lens apertures UAF1 positioned within the aperture UAO of the objective lens unit 110. The second magnification lens unit 130 may be configured to form an OCT aperture UAF2 disposed separately from the pair of magnification lens apertures UAF1 within the aperture UAO of the objective lens unit 110.

Further, the pair of first magnification lens units 120 and the second magnification lens unit 130 may include separately-arranged body tubes MT1 and MT2 that surround the side surfaces of a plurality of lenses of the pair of first magnification lens units 120 and the side surfaces of a plurality of lenses of the second magnification lens unit 130. By separating the optical system configuration (first magnification lens units 120 for the stereo microscope 12 and the optical system configuration (second magnification lens unit 130) for the OCT unit 14 in this manner, it is possible to suppress performance degradation that may occur due to the difficulty to perform the AR coating or the magnification adjustment according to each wavelength when the wavelength is changed in conformity with the wavelengths used in the respective optical systems.

The pair of magnification lens apertures UAF1 may be disposed at positions symmetrical with respect to the optical axis OAO of the objective lens unit 110. Further, the OCT aperture UAF2 may be disposed to be spaced apart from the axis CA connecting the centers of the pair of magnification lens apertures UAF1. The normal line NR extending from the center of the OCT aperture UAF2 to the axis CA may substantially perpendicularly intersect the optical axis OAO of the objective lens unit 110. Further, the positional relationship between the magnification lens apertures UAF1 and the OCT aperture UAF2 may be changed in various forms so that they do not overlap each other within the aperture UAO of the objective lens unit 110.

Further, the optical device 10 may further include an illumination unit (not shown) having an aperture UAI spaced apart from the magnification lens apertures UAF1 and the OCT aperture UAF2 within the aperture UAO of the objective lens unit 110. The normal line NR extending from the center of the aperture UAI to the axis CA may substantially perpendicularly intersect the optical axis OAO of the objective lens unit 110. Moreover, the positional relationship between the aperture UAI and the pair of magnification lens apertures UAF1 or the OCT aperture UAF2 may be changed in various forms so that they do not overlap each other within the aperture UAO of the objective lens unit 110.

The illumination unit may illuminate the target object OB in various ways so that an appropriate stereoscopic image of the target object OB can be formed. In one embodiment, the illumination unit may include an epifluorescence illumination device that irradiates the target object OB through the objective lens unit 110 with the light generated from a light source. However, this is only for the purpose of description. The present disclosure is not limited thereto. Various means for irradiating the target object OB may constitute the illumination unit. FIG. 4 is a flowchart illustrating a procedure of an optical path forming method for forming a stereoscopic image and a tomographic image of a target object according to one embodiment of the present disclosure.

Although process steps, method steps, algorithms, etc. are illustrated in a sequential order in the flowchart shown in the present disclosure, such processes, methods, and algorithms may be configured to be operated in any suitable order. In other words, the steps in the processes, methods, and algorithms explained in various embodiments of the present disclosure are not necessarily performed in the order described in the present disclosure. Further, even though some steps are explained as being performed non-simultaneously, such steps may be simultaneously performed in another embodiment. Moreover, the illustration of the processes depicted in the figure does not mean that the illustrated processes exclude other changes and modifications thereto, that any of the illustrated processes or the steps thereof is essential for at least one of various embodiments of the present disclosure, and that the illustrated processes are desirable.

As shown in FIG. 4, in step S410, an aperture of the objective lens unit having a predetermined size may be formed. For example, referring to FIGS. 1 to 3, the objective lens unit 110 of the optical device 10 may form an aperture UAO of a predetermined size. In one embodiment, the objective lens unit 110 may include a plurality of lenses to form an aperture UAO of a predetermined size indicating an area where the apertures of the plurality of lenses overlap each other.

In step S420, the magnification lens apertures may be formed so as to be located within the aperture of the objective lens unit. For example, referring to FIGS. 1 to 3, the first magnification lens units 120 of the optical device 10 may form magnification lens apertures UAF1 so as to be positioned within the aperture UAO of the objective lens unit 110. In one embodiment, the magnification lens apertures UAF1 may be formed to be symmetrical with respect to the optical axis OAO of the objective lens unit 110. However, this is only for the purpose of description. The present disclosure is not limited thereto. The magnification lens apertures may be formed in various ways so as to be located within the aperture of the objective lens unit. In step S430, there may be formed an OCT aperture positioned within the aperture of the objective lens unit and disposed separately from the pair of magnification lens apertures. For example, referring to FIGS. 1 to 3, the second magnification lens unit 130 of the optical device 10 may form an OCT aperture UAF2 located within the aperture UAO of the objective lens unit 110 and disposed separately from the pair of magnification lens apertures UAF1. In one embodiment, the OCT aperture UAF2 may be disposed to be spaced apart from the axis CA connecting the centers of the magnification lens apertures UAF1. The normal line NR extending from the center of the OCT aperture UAF2 to the axis CA may be formed to substantially perpendicularly intersect the optical axis OAO of the objective lens unit 110. However, this is only for the purpose of description. The present disclosure is not limited thereto. The OCT aperture located within the aperture of the objective lens unit and disposed separately from the pair of magnification lens apertures may be formed in various ways.

In step S440, the light received from the OCT unit may be delivered to the second magnification lens unit to form a tomography image of the target object. For example, referring to FIGS. 1 to 3, the light delivery unit 140 of the optical device 10 may deliver the light having a plurality of wavelengths received from the OCT unit 14 to the second magnification lens unit 130 to capture a tomographic image of the target object OB. In one embodiment, the light delivery unit 140 may be implemented as any type of optical element capable of delivering the light received from the OCT unit 14 to the second magnification lens unit 130. Accordingly, the light delivery unit 140 may be a component (e.g., a beam splitter) capable of performing the refraction and transmission of light. However, the present disclosure is not limited thereto. The light delivery unit 140 may be a component (e.g., folding mirror) capable of performing the refraction of light in a relatively efficient manner.

In step S450, the light received from the light delivery unit may be irradiated to the target object, and the light reflected from the target object may be delivered to the light delivery unit. For example, referring to FIGS. 1 to 3, the second magnification lens unit 130 of the optical device 10 may irradiate the light received from the OCT unit 14 through the light delivery unit 140 to the target object OB, and may deliver the light reflected from the target object OB to the light delivery unit 140.

In step S460, the light received from the second magnification lens units may be delivered to the OCT unit. For example, referring to FIGS. 1 to 3, the light delivery unit 140 of the optical device 10 may deliver the light received from the second magnification lens unit 130 to the OCT unit 14. The OCT unit 14 may form a tomography image of the target object OB by using the light received from the light delivery unit 140.

While the foregoing methods have been described with respect to particular embodiments, these methods may also be implemented as computer-readable codes on a computer-readable recording medium. The computer-readable recoding medium includes any kind of data storage devices that can be read by a computer system. Examples of the computer-readable recording medium includes ROM, RAM, CD-ROM, magnetic tape, floppy disk, optical data storage device and the like. Also, the computer-readable recoding medium can be distributed to the computer systems which are connected through a network so that the computer-readable codes can be stored and executed in a distribution manner. Further, the functional programs, codes and code segments for implementing the foregoing embodiments can easily be inferred by programmers in the art to which the present disclosure pertains.

Although the technical spirit of the present disclosure has been described by the examples described in some embodiments and illustrated in the accompanying drawings, it should be noted that various substitutions, modifications, and changes can be made without departing from the scope of the present disclosure which can be understood by those skilled in the art to which the present disclosure pertains. In addition, it should be noted that that such substitutions,

What is claimed is:

1. A stereo microscope to which an optical coherence tomography (OCT) unit for forming a tomographic image of a target object is connectable, comprising:
an objective lens unit including a plurality of lenses each having an aperture of a predetermined size;
a pair of first magnification lens units each including a plurality of lenses having a pair of magnification lens apertures and positioned within the aperture of the objective lens unit;
a second magnification lens unit including a plurality of lenses having an optical coherence tomography (OCT) aperture and disposed separately from the pair of magnification lens apertures within the aperture of the objective lens unit;
and a light delivery unit configured to receive light from the OCT unit and deliver the light to the second magnification lens unit and configured to deliver light received from the second magnification lens unit to the OCT unit,
wherein the second magnification lens unit is configured to irradiate the target object with light received from the light delivery unit and deliver light reflected from the target object to the light delivery unit; wherein the pair of magnification lens apertures are disposed at positions symmetrical with respect to an optical axis of the objective lens unit, the OCT aperture is disposed to be spaced apart from an axis connecting the pair of magnification lens apertures, and a normal line extending from the OCT aperture to the axis is configured to intersect the optical axis.

2. The stereo microscope of claim 1, wherein the pair of first magnification lens units and the second magnification lens unit include separately-arranged body tubes configured to surround side surfaces of the plurality of lenses of the pair of first magnification lens units and side surfaces of the plurality of lenses of the second magnification lens unit, respectively.

3. The stereo microscope of claim 1, wherein the light delivery unit includes at least one of a folding mirror, a beam splitter, and a prism.

4. The stereo microscope of claim 1, further comprising: an illumination unit having an aperture spaced apart from the pair of magnification lens apertures and the OCT aperture within the aperture of the objective lens unit.

5. The stereo microscope of claim 1, further comprising: a pair of ocular lens units on which a stereoscopic image of the target object received through the pair of first magnification lens units is formed, wherein the light delivery unit is disposed between the pair of ocular lens units and the second magnification lens unit.

6. An optical device, comprising: an optical coherence tomography (OCT) unit configured to form a tomographic image of a target object; and a stereo microscope configured to form a stereoscopic image of the target object, wherein the stereo microscope includes: an objective lens unit including a plurality of lenses each having an aperture of a predetermined size; a pair of first magnification lens units each including a plurality of lenses having a pair of magnification lens apertures and positioned within the aperture of the objective lens unit; a second magnification lens unit including a plurality of lenses having an OCT aperture and disposed separately from the pair of magnification lens apertures within the aperture of the objective lens unit; and a light delivery unit configured to receive light from the OCT unit and deliver the light to the second magnification lens unit and configured to deliver light received from the second magnification lens unit to the OCT unit, wherein the second magnification lens unit is configured to irradiate the target object with light received from the light delivery unit and deliver light reflected from the target object to the light delivery unit; and wherein the pair of magnification lens apertures are disposed at positions symmetrical with respect to an optical axis of the objective lens unit, the OCT aperture is disposed to be spaced apart from an axis connecting the pair of magnification lens apertures, and a normal line extending from the OCT aperture to the axis is to intersect the optical axis.

7. The optical device of claim 6, wherein the pair of first magnification lens units and the second magnification lens unit include separately-arranged body tubes configured to surround side surfaces of the plurality of lenses of the pair of first magnification lens units and side surfaces of the plurality of lenses of the second magnification lens unit, respectively.

8. The optical device of claim 6, wherein the light delivery unit includes at least one of a folding mirror, a beam splitter, and a prism.

9. The optical device of claim 6, wherein the stereo microscope further includes an illumination unit having an aperture spaced apart from the pair of magnification lens apertures and the OCT aperture within the aperture of the objective lens unit.

10. The optical device of claim 6, wherein the stereo microscope further includes a pair of ocular lens units on which a stereoscopic image of the target object received through the pair of first magnification lens units is formed, and the light delivery unit is disposed between the pair of ocular lens units and the second magnification lens unit.

11. An optical path forming method for forming a stereoscopic image and a tomographic image of a target object, comprising: forming, by an objective lens unit, an aperture of a predetermined size: forming, by a first magnification lens unit, a magnification lens aperture so as to be positioned within the aperture of the objective lens unit: forming, by a second magnification lens unit, an optical coherence tomography (OCT) aperture positioned within the aperture of the objective lens unit and disposed separately from the pair of magnification lens apertures, delivering, by a light delivery unit, light received from an OCT unit for forming the tomographic image of the target object to the second magnification lens unit: irradiating, by the second magnification lens unit, the target object with light received from the light delivery unit, and delivering, by the second magnification lens unit, light reflected from the target object to the light delivery unit delivering, by the light delivery unit, light received from the second magnification lens unit to the OCT unit and wherein the pair of magnification lens apertures are disposed at positions symmetrical with respect to an optical axis of the objective lens unit, the OCT aperture is disposed to be spaced apart from an axis connecting the pair of magnification lens apertures, and a normal line extending from the OCT aperture to the axis is to intersect the optical axis.

* * * * *